United States Patent
Guidotti et al.

[11] Patent Number: 5,941,863
[45] Date of Patent: Aug. 24, 1999

[54] ABSORBENT ARTICLES HAVING IMPROVED PROPERTIES

[75] Inventors: Ted Guidotti; Anette Buschka, both of Göteborg; Anders Gustafsson, Billdal; Urban Widlund, Pixbo, all of Sweden

[73] Assignee: SCA Mölnlycke AB, Göteborg, Sweden

[21] Appl. No.: 08/849,884

[22] PCT Filed: Dec. 27, 1995

[86] PCT No.: PCT/SE95/01587

§ 371 Date: Jun. 17, 1997

§ 102(e) Date: Jun. 17, 1997

[87] PCT Pub. No.: WO96/20670

PCT Pub. Date: Jul. 11, 1996

[30] Foreign Application Priority Data

Dec. 30, 1994 [SE] Sweden .................................. 9404582

[51] Int. Cl.[6] .................................................. A61F 13/15
[52] U.S. Cl. ........................ 604/378; 604/358; 604/374; 604/385.1
[58] Field of Search ...................... 604/378, 368, 604/379, 385.1, 374; 428/131; 128/287; A61F 13/48, 13/15, 13/46

[56] References Cited

U.S. PATENT DOCUMENTS

| | | | |
|---|---|---|---|
| 2,788,003 | 4/1957 | Morin | 604/385.1 |
| 3,889,679 | 6/1975 | Taylor | 604/385.1 |
| 4,027,672 | 6/1977 | Karami | 128/284 |
| 4,333,462 | 6/1982 | Holtman et al. . | |
| 4,333,463 | 6/1982 | Holtman . | |
| 4,333,464 | 6/1982 | Nakano . | |
| 4,413,996 | 11/1983 | Taylor . | |
| 4,443,512 | 4/1984 | Delvaux | 604/385.1 |
| 4,560,372 | 12/1985 | Pieniak . | |
| 4,643,727 | 2/1987 | Rosenbaum . | |
| 4,704,112 | 11/1987 | Suzuki et al. | 604/378 |
| 5,500,270 | 3/1996 | Langdon et al. | 428/119 |
| 5,614,283 | 3/1997 | Potnis et al. | 604/385.1 |
| 5,788,684 | 8/1998 | Abuto et al. | 604/385.1 |

FOREIGN PATENT DOCUMENTS

| | | |
|---|---|---|
| 0 124 365B1 | 10/1986 | European Pat. Off. . |
| 0 228 353 A1 | 7/1987 | European Pat. Off. . |
| WO 90/14063 | 11/1990 | European Pat. Off. ........ A61F 13/15 |
| 0 528 567B1 | 9/1996 | European Pat. Off. . |
| WO 90/14063 | 11/1990 | Sweden ......................... A61F 13/46 |
| 2 156 681 | 10/1985 | United Kingdom . |
| WO 87/01914 | 4/1987 | WIPO . |
| WO 94/10956 | 5/1994 | WIPO . |
| WO 95/07673 | 3/1995 | WIPO . |

*Primary Examiner*—Robert A. Clarke
*Assistant Examiner*—Miley Craig Peppers, III
*Attorney, Agent, or Firm*—Burns, Doane, Swecker & Mathis, L.L.P.

[57] ABSTRACT

An absorbent article which includes a liquid-permeable outer sheet (1) disposed on a first surface of the article, a liquid-impermeable outer sheet (2) disposed on a second surface of the article, and an absorbent body (3) which is enclosed between the two casing sheets and which includes a receiving space (24) for taking-up body liquid, wherein the space is comprised of at least one cavity or region of lower density than the density of a part of the absorbent body (3) adjacent the receiving space (24) and located generally in the same plane. The article is mainly characterized in that the receiving space (24) is disposed in a storage layer (19) in the absorbent body (3), and in that parts (20,125) of the storage layer (19) adjacent the receiving space (24) include a material which when wetted increases in volume in a direction generally perpendicular to the first surface of the article, whereby the size of the receiving space (24) is also increased in this direction as a result of wetting the article.

19 Claims, 4 Drawing Sheets

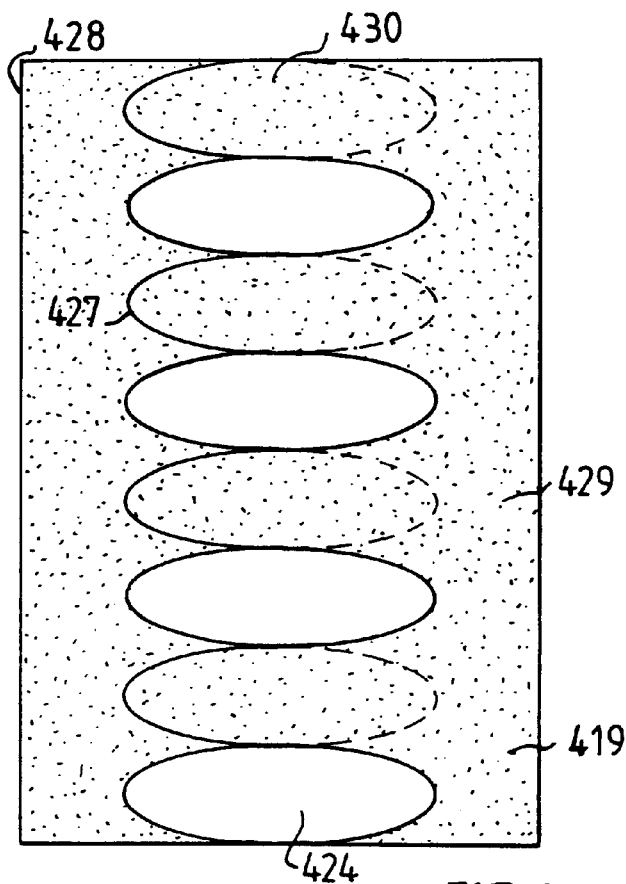
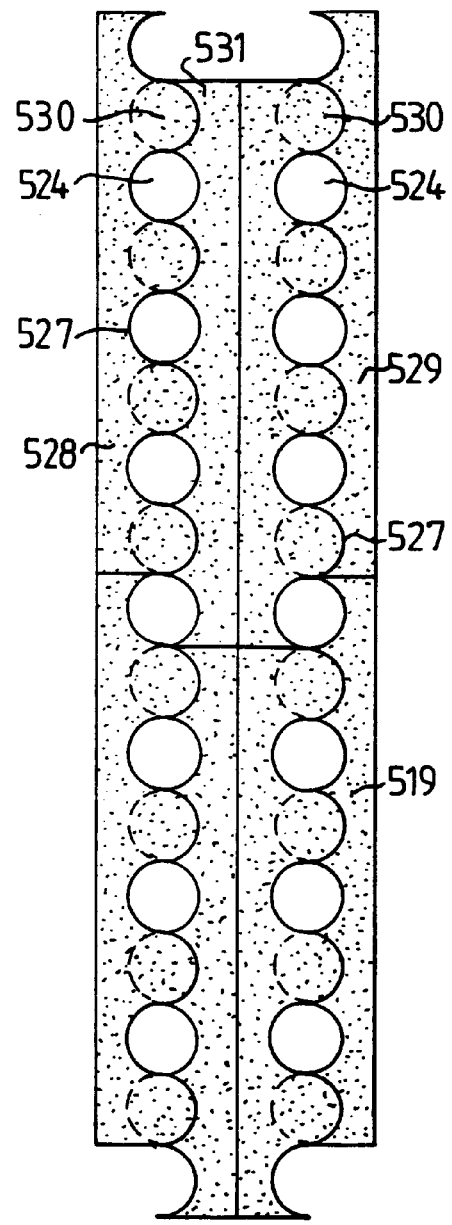
FIG. 8
FIG. 9

ABSORBENT ARTICLES HAVING IMPROVED PROPERTIES

The present invention relates to an absorbent article which includes a liquid-permeable casing sheet disposed on a first article surface, a liquid-impermeable casing sheet disposed on a second article surface, and an absorbent body which is enclosed between the two casing sheets and which includes a receiving space in which body liquid is taken up, said space consisting in at least one cavity or one region of lower density than those parts of the absorbent body which border on the receiving space and which lie generally in the same plane.

Hitherto, the problem encountered with absorbent articles, such as diapers, pants-type diapers, incontinence guards, sanitary napkins or like articles which are intended to repeatedly receive and absorb body liquid, or fluid, discharged by a user is that the rate at which the liquid is able to penetrate into the article decreases considerably with each new wetting occasion. This problem is particularly pronounced in diapers and incontinence guards that are intended for children and adults, since in these cases the quantities of liquid that the article will receive and absorb are relatively large and are discharged within the space of only a few seconds. It is therefore not unusual, particularly after a first wetting of the article, that the liquid which is not immediately released into the article will instead flow over the surface of the article and leak past the edges thereof. Such leakage of body liquid is naturally highly undesirable, since it is liable to soil the clothes, bed linens and mattresses used by the wearer, and even stain and destroy such commodities.

The reason why the body liquid penetration rate decreases with repeated wetting of the article is because the absorbent body of the article becomes saturated with body liquid temporarily within a limited area around the area on the article surface in which the body liquid first impinges, the so-called primary wetting area. The absorbent articles are normally comprised of one or more layers of hydrophilic fibres, for instance cellulose fluff pulp, and often also include a powerful absorbing hydrocolloidal material, so-called superabsorbents. Liquid is transported relatively slowly through such materials, since transportation of the liquid is mainly caused by the capillary forces acting in the cavities located between fibres and particles in the absorbent body of the article. Liquid is transported within the hydrocolloidal materials by diffusion, which is a still slower process than the process generated by the capillary forces. The liquid will therefore remain in the primary wetting area of the article for a relatively long period of time and will then gradually be transported out to surrounding parts of the absorbent body.

The problem has been accentuated in recent years, since development has tended towards absorbent bodies which have been compressed to greater and greater degrees of compression with the intention of reducing packaging volume and for reasons of transportation, storage and environment.

It is known to provide the article with liquid-transporting means in the form of compressed patterns, for instance compressed stripes, which function to disperse the liquid in the longitudinal direction of the article, so as to steer the transportation of liquid away from the primary wetting area to parts of the absorbent body in which absorbent material is still unused. An article possessing such compressed stripes is earlier known from PCT/SE94/00835. Liquid transportation in the article is mainly the result of the differences in capillary forces acting between the compressed stripes and surrounding material. Even though a positive effect is obtained in this case in the form of a directed liquid flow in the absorbent body, the rate at which liquid is transported in the article is much too slow in relation to the rate at which body liquid is discharged to the article. Consequently, there is a risk that the liquid will not be absorbed quickly enough, but instead will run along the surface of the article and out over the edges thereof, resulting in leakage, this risk being particularly manifest in products which are intended for urine absorption, such as diapers and incontinence guards, onto which large quantities of liquid are often discharged over a short period of time. Furthermore, heavy compression of the article results in rigid parts which do not flex easily and which prevent the article from following satisfactorily the movements of the wearer's body and conforming to shape of the wearer's body in use.

Another method of improving the ability of an absorbent article to receive and retain large volumes of body liquid is to create different types of liquid-receiving cavities, or basins, in the article.

U.S. Pat. No. 3,889,679 describes a diaper having a plurality of circular holes disposed through the absorbent body of the diaper. Since a diaper, however, is wetted within a limited area of the diaper, the primary wetting area, only those holes that are located nearest this area will be utilized in initially taking-up body liquid. These holes are quickly filled with liquid and are then subsequently drained to the surrounding absorbent material, by virtue of the liquid being drawn by suction away from the holes by the capillary forces acting between the fibres in the absorbent material. As mentioned above, this process is a slow process, and there is a considerable danger than the holes will still contain liquid on the occasion of the next wetting of the absorbent body. Furthermore, the absorbent material located nearest the primary wetting area of the diaper will gradually become saturated with body liquid and therewith lose all ability to drain liquid away from the holes in use. Another drawback with the absorbent body is that it is comprised of a material which collapses when wetted and generally loses its three-dimensional structure. As a result, the availability of a cavity in the absorbent body to take up liquid is practically non-existent after the first wetting.

Swedish Patent Application No. 9304321-4 describes an absorbent body for absorbent articles such as diapers, incontinence guards and sanitary napkins, which is provided with a liquid-receiving part in the form of a well which is located generally opposite the anticipated primary wetting region of the absorbent body and which extends depth-wise into and through a liquid storage part in the absorbent body. The well is in liquid communication with a liquid-dispersion layer disposed beneath a liquid storage layer and has a larger effective mean pore size than the surrounding liquid storage part.

An absorbent body of this kind will function extremely effectively when receiving a first liquid quantity and also when receiving subsequent liquid quantities, provided that the time lapse between successive liquid discharges is sufficient for the well to empty of liquid between these discharge occasions. The absorbent body according to Swedish Patent Application No. 9304321-4 also depends on the effect of capillary forces to drain liquid from the well. The liquid-receiving well is therefore emptied gradually as liquid is transported from the coarser pores in the well to the finer pores in the surrounding absorbent material. There is also a danger than the well will be too small to accommodate large quantities of liquid discharge, causing the well to overfill.

Publications WO 87/01914, U.S. Pat. No. 4,333,462, U.S. Pat. No. 4,333,463, U.S. Pat. No. 4,333,464, U.S. Pat.

No. 4,413,996, E.P. 0,124,365, G.B. 2,156,681, U.S. Pat. No. 4,643,727 and E.P. 0,528,567 also describe similar articles provided with cavities or basin-shaped hollows for receiving and collecting liquid.

There is thus a serious need for an absorbent article which will permit repeated wettings at high penetration rates with regard to liquid discharged on the subsequent wetting occasions.

According to the invention, there is provided an article of the kind defined in the introduction in which the drawbacks of earlier known articles of this kind have essentially been eliminated.

The inventive article is primarily characterized in that the receiving space is provided in one storage layer of the absorbent body, and in that those parts of the storage layer that border on the receiving space include a material which when wetted increases in bulk in a direction generally perpendicular to the first surface of the article, whereby the size of the receiving space also increases in said direction when wetting the article.

According to one embodiment of the invention, the liquid-receiving space is comprised of one or more holes or regions of lower density than the density of the surrounding material in the storage layer which extend through at least a part of the thickness of the storage layer.

According to another embodiment, the storage layer is comprised of at least two separate bodies of material which extend in the form of column-like spacing means generally perpendicular between two further layers of material in the article, and together with these material layers delimit a continuous receiving space between the material layers. The separate bodies of material may, for instance, comprise superabsorbent material enclosed between the tubular casing extending between the two material layers, whereby swelling of the superabsorbent material through gel formation upon absorption of body liquid is only able to take place within the tubular casings, in a direction generally perpendicular to the two material layers. However, the bodies are preferably comprised of the materials described in WO 94/10956.

According to another embodiment of the invention, the receiving space is comprised of at least one channel-like cavity which extends in the longitudinal direction of the article.

According to yet another embodiment of the invention, the storage layer is formed from a web of material which is divided in the longitudinal direction of the web along a undulating curve, wherein the web-parts are displaced in relation to one another in the plane of the web, at least in the longitudinal direction of said web, whereby the web-parts define the receiving space therebetween in the plane of the web. By an undulating curve is meant a curve of any desired curve shape, such as a sinusoidal curve, a sawtooth-shaped curve, a square-wave shaped curve, etc. The amplitude of the undulations or waves, and their lengths may vary along the curve. The undulations may extend in a straight, curved or wavy line.

When the web-parts are mutually displaced by one-half wavelength in the longitudinal direction of the web, the web-parts will define therebetween a row of generally circular or oval holes alternating with overlapping web-parts extending in the longitudinal direction of the web. The size of these holes can be adjusted or controlled by displacing the web-parts towards one another. The more the web-parts are displaced towards one another, the smaller the remaining holes between the band-parts. The case in which the band-parts do not delimit cavities therebetween is not included by the invention. The size of the holes can be varied by varying the amplitude of the waves along the web, for instance so that the holes in the wetting area will be larger than the holes located outside the wetting area.

When the web-parts are displaced away from one another, in the transverse direction of the web, the storage layer will present a channel-like undulating space which extends between the web-parts.

A storage layer which is particularly suited for use in an inventive article is formed from a material in particle form which includes flash-dried cellulose fibres which have been dry-formed to a web having a surface weight of 30–2000 g/m$^2$ and compressed to a density of between 0.2–1.2 g/cm$^3$, this web being incorporated in the article without subsequent defibration and fluff formation.

Another storage layer which is particularly suited for use in accordance with the invention is formed from an air-laid web of cellulose fibres which has been compressed to a dry-formed sheet having a first density of between 0.2–1.2 g/cm$^3$, wherein the sheet is thereafter softened mechanically to a second density which is lower than the original density and therewith delaminated, so as to form a plurality of incompletely separated thin fibre layers, each of which has a density corresponding to the first density.

Another conceivable storage layer is formed from a material layer having a first thickness and containing resilient material, this layer having been pressed together perpendicularly to a plane that extends through the layer to a second thickness, and having been bound in its compressed state with a binder which is soluble in body liquid, wherein binding of the layer ceases when the layer is wetted and the reservoir layer returns at least partially to the first thickness. A storage layer of this kind may, for instance, be formed from a compressed foam material which will expand in thickness when wetted, or from a compressed fibre layer which is comprised at least partially of fibres that have a given resiliency in a wet state.

According to another embodiment of the invention, that part of the volume of the storage layer which is comprised of the receiving space is largest within the primary wetting area of the article, i.e. the area of the article which is intended to be wetted first by discharged body liquid. That part of the receiving space which takes up the storage layer volume can therewith decrease in a direction away from the primary wetting area.

The invention also relates to an absorbent body for use in an absorbent article which includes a receiving layer of soft, preferably resilient material having high liquid-permeability and a low liquid dispersion ability, and a liquid storage structure disposed inwardly of the first layer. The inventive absorbent body is characterized in that the liquid storage structure includes a storage layer which includes a storage space for taking-up body liquid and comprising at least one cavity or region of lower density than the storage layer in general, wherein parts of the storage layer that border on the receiving space include a material which when wetted increases in bulk in a direction generally perpendicular to the plane of the layer, whereby the size of the receiving space also increases in said direction as a result of wetting of the article; and in that the liquid storage structure also includes a liquid-dispersion layer of material having a high liquid dispersion capacity, wherein the storage layer is disposed between the receiving layer and the liquid-dispersion layer.

Because the storage space in an inventive article will expand in pace with the article being wetted by body liquid, the article is able to maintain a high penetration rate with regard to the liquid discharged onto the article, throughout the whole of its use period. Distinct from the earlier known articles, there can be no dramatic decrease in the penetration rate since a new liquid-receiving space is constantly created. In favourable instances, the inventive article is able to maintain essentially the same liquid penetration rate even after a plurality of wetting occasions. In particularly favourable instances, the liquid penetration rate can even increase after the first wetting occasion.

In order to achieve full effect of the expanding storage space in an inventive absorbent body, it is important that at least the layer of material arranged in abutment with that side of the storage layer which lies proximal to the liquid-permeable surface of the article has such resilience and stiffness, in both a wet and a dry state, that it will not collapse and fall into the receiving space of the storage layer, since otherwise a large part of the space available for further liquid take-up would be lost.

Those cavities, low density regions, channels, or like configurations which together form the receiving space of the article will preferably not have a dimension in the plane of the storage layer that exceeds 35 mm and preferably not exceeds 20 mm. By this is meant that each such cavity, low density region, channel or like configuration will not have an extension anywhere in the plane of the storage layer that will enable the layer to accommodate within its surface a circle having a diameter greater than 35 mm and preferably not greater than 20 mm. With larger dimensions, it is difficult to avoid the layer buckling into the receiving space and therewith diminishing the space, because of the flexibility of the material. When the absorbent article is worn, the article is curved and shaped to the shape of the wearer's body. The layer of material arranged on the side of the storage layer that lies proximal to the wearer, for instance a liquid-permeable casing sheet, will therewith tend to curve into the receiving space. This downward curving or bulging will generally increase when the material in the casing sheet is wet, but is even more pronounced in large cavities or hollows in the storage layer. Naturally, this downward bulging can be reduced by using a stiffer layer of material nearest the storage layer. However, the limit as to just how stiff this material layer may be is determined by the requirements placed on shapability, flexibility and comfort of the article in use. The smallest functional dimension of a cavity or the like in the storage layer corresponds approximately to the size of a water droplet. A cavity or some corresponding space in the storage layer should not therefore be so small that nowhere within its defining edges in the plane of the storage layer can a circle having a diameter of 3 mm or more can be inscribed.

BRIEF DESCRIPTION OF THE DRAWINGS

The invention will now be described in more detail with reference to the accompanying drawings.

FIG. 8 illustrates a storage layer having centrally disposed openings alternating with overlapping regions of material.

FIG. 9 illustrates a web of material for producing a storage layer.

Figure 1:
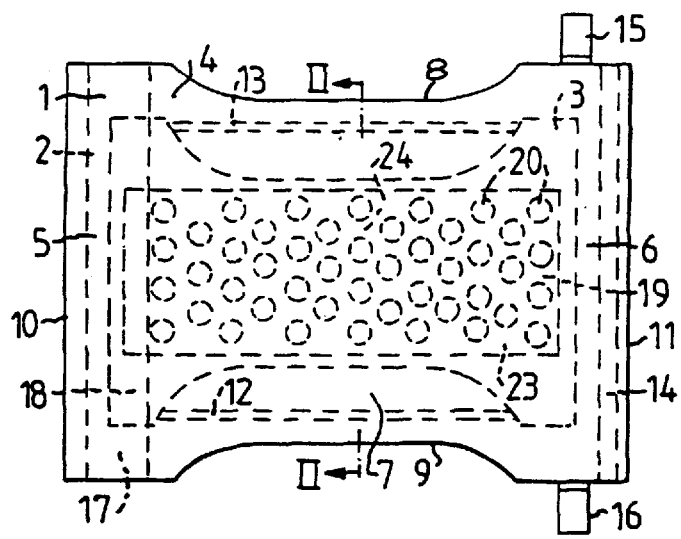
FIG. 1 illustrates from above a diaper according to a first embodiment of the invention, which includes a storage layer formed from separate bodies of material.
Figure 2A:
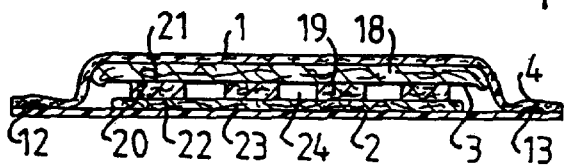
FIG. 2a is a sectional view of the diaper shown in FIG. 1 taken on the line II—II in said Figure, prior to wetting of the diaper.
Figure 2B:
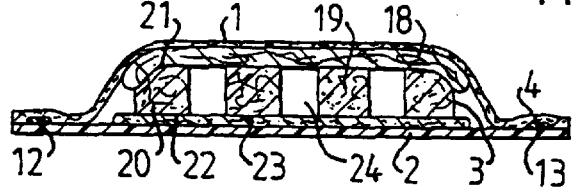
FIG. 2b is a sectional view of the diaper shown in FIG. 1 taken on the line II—II in said Figure, subsequent to wetting of the diaper.

The diaper illustrated in FIGS. 1, 2a and 2b is seen from the side which lies proximal to the wearer in use. The diaper is shown extended in a flat state and includes a liquid-permeable first casing sheet 1, made for instance of non-woven material, woven material, perforated plastic film or net mounted on that side of the diaper which is intended to lie proximal to the wearer in use. A liquid-impermeable second casing sheet 2 made, for instance, of plastic film or a nonwoven material or woven material that has been made hydrophobic, is mounted on that side of the diaper which is intended to lie distal from the wearer in use. The two casing sheets 1, 2 embrace an absorbent body 3 and are mutually joined together at parts 4 of the casing sheets 1, 2 that project out around the absorbent body 3.

The diaper is constructed so that it will embrace the lower part of the wearer's torso in a pants-like fashion when in use. To this end, the diaper has a front part 5 which, in use, is intended to face forwardly of the wearer and lie over the wearer's stomach, a rear part 6 which, in use, is intended to face rearwardly of the wearer and lie in abutment with the wearer's buttocks, and a crotch part 7 disposed between the front part 5 and the rear part 6 of the diaper and intended, in use, to be located in the crotch area between the wearer's thighs. The diaper has a generally hourglass shape, wherein its front part 5 and rear part 6 are broader than the crotch part 7. The diaper also includes two longitudinally extending side-edges 8, 9 and a front waist edge 10 and a rear waist edge 11. When the diaper is worn, the longitudinally extending side-edges 8, 9 form the edges or borders of the leg openings of the diaper, whereas the waist edges 10, 11 together embrace the waist of the user and form the waist edge or border of the diaper.

An elastic device 12, 13 is mounted along each respective side-edges 8, 9 of the diaper. The elastic devices 12, 13 are mounted on the diaper in a stretched state and when contracting gather in the side-edges 8, 9 of the diaper and curve the diaper into a trough-like shape. The effect of the elastic devices 12, 13 is not apparent from FIG. 1, however, since the diaper is shown in a flat state with the elastic devices 12, 13 in a stretched state. In use, the elastic devices 12, 13 function to hold the edges of the diaper leg openings in sealing abutment with the wearer's thighs. A further elastic device 14 is mounted along the rear waist edge 11 of the diaper, so as to obtain sealing abutment with the edge of the waist opening in a corresponding manner. Several different types of elastic devices 12–14 suitable for this purpose are known to the art, such as elastic threads, elastic bands, elastic nonwoven, or like materials.

In order to enable the diaper to be secured in use in a pants-like form around the wearer's body, a fastener tab 15, 16 is provided on each side-edge 8, 9 in the proximity of the rear waist edge 11. The fastener tabs 15, 16 are intended to coact with and fasten against a fastener receiving region 17 provided on the front diaper part 5. The fastener tabs 15, 16 are normally in the form of self-adhesive tapes which prior to use are folded over with the adhesive-coated surface lying against and protected by a fastener tab area that has been treated with a release agent, or on the diaper itself. The receiving region 17 is comprised of a reinforced region of the liquid-impermeable casing sheet 2 on the front part 5 of the diaper. This reinforcement is simplest achieved by laminating a plastic film strip on that side of the liquid-impermeable casing sheet 2 that lies distal from the absorbent body 3. This reinforcement of the receiving region 17 enables the diaper to be opened and resealed without tearing the liquid-impermeable casing sheet 2.

Alternatively, the fastener tabs 15, 16 may comprise any appropriate type of mechanical fastener means, such as one part of a Velcro® tape fastener, a press stud or equivalent means. In this regard, the receiving region 17 will be comprised of the corresponding part of the mechanical fastener device. It is also known to use fastener means which can be considered essentially as hybrids between adhesive fastener devices and mechanical fasteners. An example in this regard is described in EP-A-393,953. No fastener devices are required in the case of diapers which are intended to be supported as inserts in a pair of tightly fitting pants. So-called pants-type diapers, or trainers, also normally lack fastener devices.

The absorbent body 3 includes a first absorption layer, the liquid or fluid-receiving layer 18, which has essentially the same shape and size as the diaper itself and which is located nearest inwardly of the liquid-permeable casing sheet 1. The liquid-receiving layer 18 is suitably comprised of a soft material of high liquid-permeability and having relatively large pores or capillaries. An example of such material is lightly compressed cellulose fluff layers, in particularly comprised of mechanical, thermomechanical or chemithermomechanical (CTHP) pulp, or fibre mats and waddings of other kinds comprised of natural fibres or of synthetic fibres. Mixtures of cellulose fluff pulp, or other cellulose based fibres, with different types of synthetic fibres may also be used. It is also possible to use soft perforated or open-cell foam material. Such material has a low liquid dispersion capacity, whereby the wet area of the layer will remain restricted essentially to the primary wetting region even after repeated wetting of the layer or sheet. The wearer thus feels the surface of the diaper in contact with the wearer to be dry and comfortable against the skin, even after having worn the diaper for a relatively long time.

When the diaper is in use, the receiving layer 18 is intended to receive discharged body liquid and to transport the liquid away from the liquid-permeable casing sheet 1 and will therefore have large pores which offer as little resistance as possible to the liquid flow. The receiving layer 18 will preferably also be soft and comfortable against the wearer's skin during the full period of use. The properties of the material in the receiving layer 18 will preferably not therefore change essentially after being wetted. It is also desirable for the material to have a given resiliency, so that it will endeavour to return to its original state after being compressed or wrinkled, pleated, in use.

When the receiving layer 18 includes cellulose fibres which normally have a relatively low resiliency in a wet state, for instance chemical pulp, it may be suitable to admix the cellulose fibres with another material which will enhance the wet resilience of the material and therewith impart to the first absorption layer a given degree of resiliency even in a wet state. Examples of such materials include different types of thermoplastic fibres or particles which, when the layer is heated, will function to bind the fibres in the layer and therewith fixate the fibres in their mutual positions and therewith impart to the layer a higher tensile strength and improved resiliency in both a wet and a dry state. Cellulose fibres can also be modified chemically, e.g. by cross-linking, thereby to enhance their inherent resiliency, or by mixing the cellulose fibres with highly resilient synthetic fibres.

The receiving layer 18 may also include a minor quantity of so-called superabsorbents, i.e. material in the form of fibres, particles, granules, film or the like which is able to absorb and bind body liquid in an amount corresponding to several times the intrinsic weight of the superabsorbents while chemically forming an hydraulic gel.

Seen from the liquid-permeable casing sheet 1, there is provided inwardly of the receiving layer 18 a second absorption layer 19 which is intended to be able to receive and collect relatively large quantities of body liquid over a short period of time. The second absorption layer, the storage layer 19, is comprised of a number of cylindrical bodies 20 whose one flat surface 21 abuts with the receiving layer 18 and whose other flat surface 22 abuts a third absorption layer 23 which is located inwardly of the storage layer 19, nearest the liquid-impermeable casing sheet 2. The cylindrical bodies 20 are spaced mutually apart and leave therebetween a continuous cavity 24 in which body liquid discharged to the diaper can collect.

The diaper illustrated in FIG. 1 has its main extension in the XY plane, the X direction being defined by the transverse direction of the diaper and the Y direction being defined by the longitudinal direction of the diaper. The cylindrical bodies 20 are comprised of a material which when wetted with body liquid will expand strongly in the Z direction, i.e. in a direction perpendicular to the XY plane. The manufacture of a particularly suitable material of this kind is described in WO 94/10956. One characteristic feature of this material is that it is produced by dry-forming flash dried cellulose fibres to produce a web having a surface weight of 30–2000 g/m$^2$, which is compressed to a density of between 0.2–1 g/cm$^3$, and that the web is incorporated as an absorbent structure in an absorbent article without subsequent defibration and fluff formation. Another suitable expanded material is cellulose fluff pulp which has been admixed with a given quantity of superabsorbent material, preferably at least 10 percent by weight superabsorbent material. The aforedescribed materials are often produced in the form of relatively thin webs, having a thickness of only a few millimeters. The cylindrical bodies can therewith be formed from one or more layers of such material.

Other suitable materials for producing the cylindrical bodies are compressed foam materials or fibre waddings which when wetted will return at least partially to their non-compressed size. When desired, the materials may be fixed in their compressed states with the aid of some type of water-soluble binder. It is also conceivable to use superabsorbent material enclosed in tubular casings that are oriented so that the superabsorbent material will swell and fill the casing in the Z direction of the diaper when absorbing liquid.

The aforedescribed examples of suitable wet-expanding materials are merely intended to illustrate the invention and shall not be considered to limit its scope. However, the wet-expanding material shall be capable of expanding in the Z direction to at least twice its dry-state extension in said direction, when saturated with body liquid.

The third absorption layer 23, hereinafter referred to as the liquid-dispersion layer 23, is comprised of a high density material which also has a high liquid dispersion and liquid retention capacity. Similar to the cylindrical bodies 20 in the storage layer 19, the material described in WO/9410956 is particularly usable in this regard. However, conventional compressed layers of cellulose fluff pulp, absorbent foam material, or different kinds of tissue laminates may be used. The liquid-dispersion layer 23 is generally rectangular in shape and has a smaller extension in the XY plane of the diaper than the receiving layer 18. The liquid-dispersion layer will therefore be surrounded on all sides by a soft, body-friendly material of low liquid dispersion ability. This arrangement affords several advantages. Firstly, no sharp or hard edges on the liquid-dispersion layer 23 are able to come into contact with the wearer's body and chafe or irritate the wearer's skin; and, secondly, any movement of liquid conducted towards the diaper edges in the liquid-dispersion layer 23 is counteracted, therewith considerably reducing the danger of body liquid leaking from the diaper. The edges of the liquid-dispersion layer 23 also form fold indications or directives around which the diaper is able to fold when compressed in the crotch region between the wearer's thighs in use. In this way, the diaper will take a size and shape which is better adapted to the space in the crotch region.

The liquid-dispersion layer 23 is primarily intended to transport body liquid away from that region of the diaper on which the body liquid is first received, i.e. the primary wetting area. The absorbent material in the absorbent body 3 is utilized more effectively in this way. This is achieved by compressing the liquid-dispersion layer 23 relatively heavily, wherewith the layer obtains a high affinity to body liquid and a high liquid dispersion capacity. For the purpose of guiding liquid transportation in the longitudinal direction of the diaper, the liquid-dispersion layer 23 may conveniently be provided with a longitudinally extending compression profile or pattern, in the form of grooves, wave patterns, or like configurations.

The liquid-dispersion layer 23 may also advantageously include some form of superabsorbent. The amount of superabsorbent used in the liquid-dispersion layer 23 is preferably greater than the amount used in the liquid-receiving layer 18, since, distinct from the receiving layer 18, the liquid-dispersion layer 23 is intended to absorb and retain the body liquid discharged to the diaper.

The cylindrical bodies 20 in the storage layer 19 are suitably fixed to the liquid-dispersion layer 23, for instance glued thereto, in order to avoid movement of the cylindrical bodies 20 in the diaper. Alternatively, the cylindrical bodies 20 may be fastened to a separate layer, for instance a layer of tissue or nonwoven material, or may be fastened to the liquid-receiving layer 18. Naturally, the cylindrical bodies 20 may be fastened to more than one layer.

All of the absorption layers 18, 19, 23 in the absorbent body 3 are in direct liquid communication with one another. Thus, liquid can always be transported to the storage layer 19 of the diaper in a direction generally perpendicular to the casing sheet 1, irrespective of where liquid impinges on the liquid permeable casing sheet 1 of the diaper.

As shown in FIG. 2a, the storage layer 19 has a relatively small thickness prior to the diaper absorbing body liquid. The cavity 24 formed between the cylindrical bodies 20 on the diaper in FIG. 2a, however, is sufficient to receive the amount of liquid first discharged. The liquid discharged to the diaper will impinge on the liquid-permeable casing sheet 1 thereof within a small limited area, the so-called primary wetting area.

The location of the primary wetting area on the diaper will vary slightly between different users. This variation is due to differences in body shape and will also depend on the sex of the wearer. Male wearers tend to wet the diaper at a location further forwards than a female user. The location of the primary wetting area of the diaper can also vary to some extent with one and the same user during use, as a result of movement of the wearer and the attitudes assumed by the wearer's body. The wetting area of the illustrated diaper cannot therefore be determined in a meaningful manner. However, the primary wetting area is somewhere in the diaper crotch part 7.

The body liquid passes quickly down through the casing sheet 1 and the receiving layer 18. It is important that the material in the receiving layer 18 has a resiliency and stiffness which will prevent the layer from collapsing and falling into the cavity 24 in the storage layer 19, even after becoming wet, since a large part of the space available for receiving liquid would then be lost.

Liquid that has passed through the receiving layer 18 collects in the cavity 24 between the cylindrical bodies 20 in the storage layer 19, and in the fibre structure proximal to the primary wetting area of the diaper. The liquid is then spread further out in the XY plane of the diaper by the absorbent material in the liquid-dispersion layer 23. This absorption process is relatively slow, since it depends on the capillary forces acting between fibres and particles in the absorption material. The fibre structure nearest the wetting area will, in general, not have had time to be emptied of liquid before liquid is again discharged to the diaper.

However, a part of the liquid collected in the cavity 24 in the storage layer 19 in conjunction with the first wetting occasion will be absorbed by the cylindrical bodies 20. Since the material in the cylindrical bodies 20 expands in the Z direction of the diaper when wetted, this expansion will cause the receiving layer 18 and the dispersion liquid layer 23 to move apart in the Z direction, thereby enlarging the cavity 24 between the two absorption layers 18, 19. Consequently, when the diaper is next wetted the space available for instantaneous take-up of liquid will be equally as large or larger than the space that was available on the first wetting occasion. Thus, the rate at which liquid penetrates into the diaper will not decrease to any appreciable extent, but may even increase with repeated wetting of the diaper absorbent body 3.

Since the cavity 24 in the storage layer 19 is continuous or coherent between the cylindrical bodies, the liquid that penetrates through the receiving layer 18 will flow-out over a relatively large area around the primary wetting area. Liquid is absorbed into the liquid-dispersion layer 23 relatively slowly owing to the compact structure of said layer, whereby a large part of the liquid is able to run on the surface of the layer that faces towards the cavity 24 and therewith be spread over a considerable area before being absorbed by the liquid-dispersion layer 23 or by the cylindrical bodies 20 in the storage layer 19. In this way, it is not only those cylindrical bodies 20 that are located nearest the primary wetting area which will be wetted by the liquid and swell in the Z direction, but that such expansion will also be observable at a distance from the wetting area. Liquid is dispersed further into the diaper by liquid transportation in the liquid-dispersion layer 23. Thus, liquid can subsequently be absorbed from the liquid-dispersion layer 23 to the cylindrical body surfaces 22 in abutment with said liquid-dispersion layer 23 and belonging to cylindrical bodies 20 that are located outside the diaper area reached by the liquid flowing out on the surface of the liquid-dispersion layer 23. This first wetting occasion therewith starts a process which in time also causes those cylindrical bodies 20 that are located distal from the wetting area to gradually be wetted and expand in the Z direction of the diaper.

Figure 3:
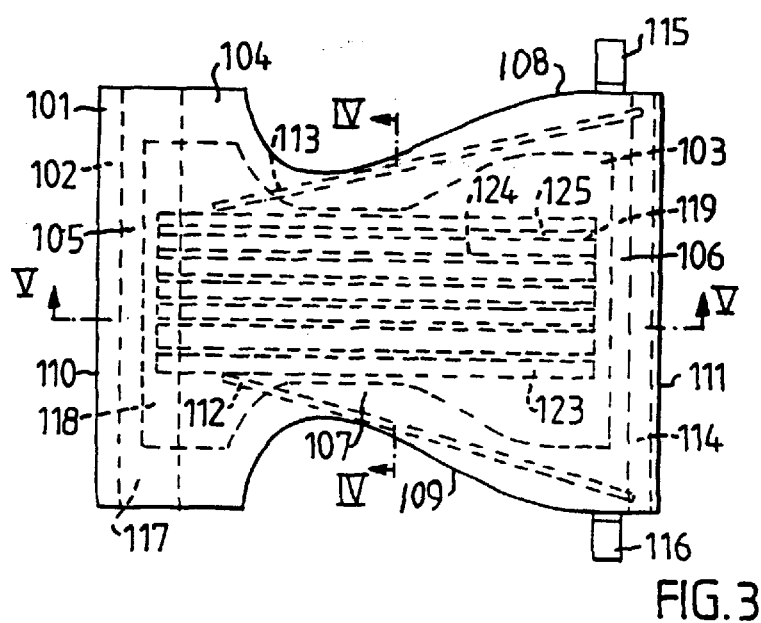
FIG. 3 illustrates from above a diaper according to a second embodiment of the invention, including a storage layer comprised of longitudinally extending, swellable strips of material.
Figure 4A:
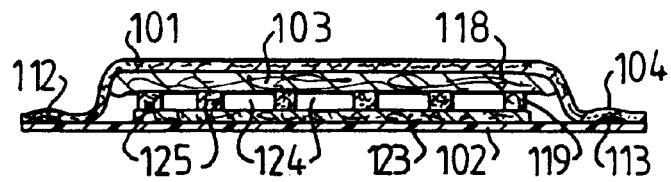
FIG. 4a is a cross-sectional view of the diaper shown in FIG. 3, taken on the line IV—IV, prior to wetting of the diaper.
Figure 4B:
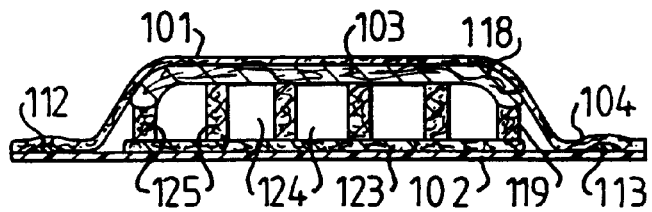
FIG. 4b is a cross-sectional view of the diaper shown in FIG. 3, taken on the line IV—IV, subsequent to wetting of the diaper.
Figure 5:
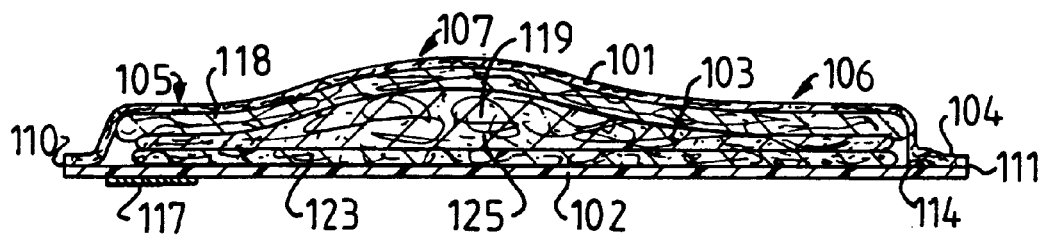
FIG. 5 is a longitudinal section view of the diaper shown in FIG. 3, taken on the line V—V, subsequent to wetting of the diaper.

The diaper illustrated in FIGS. 3–5 has principly the same construction as the diaper shown in FIG. 1 and includes an absorbent body 103 enclosed between a liquid-permeable casing sheet 101 and a liquid-impermeable casing sheet 102. The diaper has a front part 105, a rear part 106 and an intermediate crotch part 107 and also has two longitudinally extending side edges 108, 109 and a forward waist edge 110 and a rear waist edge 111. The diaper is generally T-shaped with the cross-member of the T forming the front part 105 of the diaper and with the column of the T gradually increasing in width from the diaper crotch part 107 and over the rear diaper part 106 towards the rear waist edge 111.

Elastic devices 112, 113 are mounted along the side edges 108, 109 of the diaper in a V-shaped pattern diverging from the forward waist edge 110 towards the rear waist edge 111. A fastener tab 115, 116 is provided on each side edge 108, 109, on the rear part 106, close to the rear waist edge 111, and a corresponding fastener receiving region 117 is provided on the outside of the liquid-impermeable casing sheet 102 at the front diaper part 106, close to the forward waist edge 110.

The diaper absorbent body 103 includes a liquid-receiving layer 118 of the same kind as that used in the FIG. 1 embodiment and having essentially the same format as the diaper. A storage layer 119, which comprises a plurality of longitudinally extending strips 125 of material that can swell in the Z direction of the diaper when wetted with body liquid is disposed inwardly of the receiving layer 118, as seen in a direction from the liquid permeable casing sheet 101. Located between the strips 125 are elongated liquid-receiving cavities or channels 124. The tapes 125 are glued or likewise fastened to a liquid-dispersion layer 123 of the same kind and shape as the liquid-dispersion layer 23 used in the diaper shown in FIG. 1.

As can best be seen from FIG. 4a, the channels 124 between the strips 125 extending longitudinally in the storage layer 119 are relatively shallow prior to wetting of the diaper. However, the height of the strips 125 is sufficient for the diaper to be able to receive a first liquid quantity without liquid flowing out past the diaper edges 108–111. The liquid that penetrates into the diaper is able to run quickly away from the primary wetting area and flow out over the surface of the liquid-dispersion layer 123 in the channels 124 between the longitudinally extending strips 125. The liquid can then be absorbed gradually by the longitudinally extending strips 125 from the channels 124 and by the liquid-dispersion layer 123. Part of the liquid impinging on the diaper and penetrating down through the receiving layer 118 will, of course, wet directly those parts of the strips 125 in the storage layer 119 that are located in the primary wetting area of the diaper, these strip parts immediately beginning to swell in the Z direction of the diaper. Wetting of the strips 125 located at a distance from the primary wetting area will not commence until a certain length of time has lapsed and the liquid has been able to run out into the channels 124. The time delay or time lapse in wetting those parts of the strips 125 that lie still further away within parts of the absorbent body 103 which are not wetted until liquid has been transported in the capillaries in the liquid-dispersion layer 124 is still greater. FIG. 5 illustrates how the liquid is spread in the longitudinal direction of the diaper, by virtue of the longitudinally extending strip 125 shown in cross-section having expanded to different extents in the Z direction of the diaper, depending on the distance from the primary wetting area. FIG. 4b illustrates how liquid is spread in the cross-direction of the diaper in a similar manner.

Figure 6:
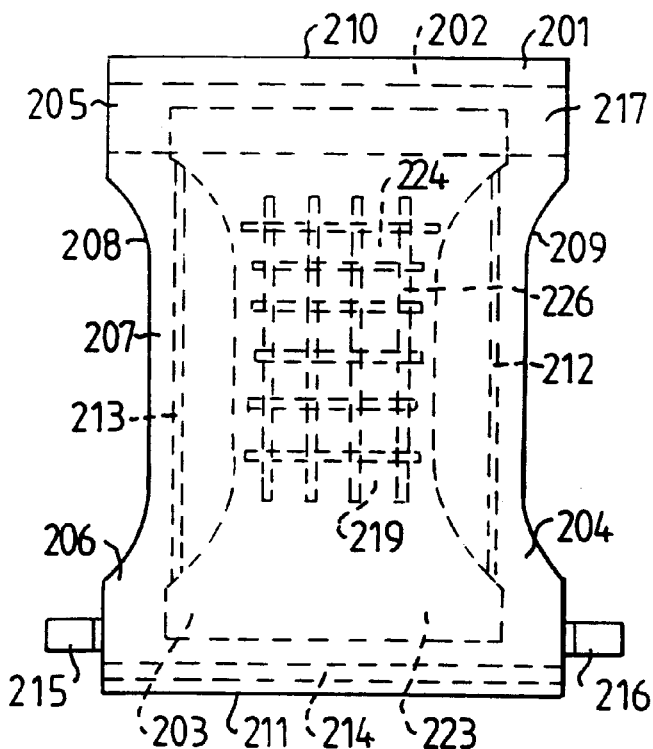
FIG. 6 is a view from above of a diaper having a net-like storage layer.

The diaper illustrated in FIG. 6 has essentially the same construction as the diapers shown in FIGS. 1–5, with an absorbent body 203 enclosed between a liquid-permeable casing sheet 201 and a liquid-impermeable casing sheet 202. The diaper has generally an hourglass shape, including a front part 205, a rear part 206 and an intermediate, narrower crotch part 207, and also includes two longitudinally extending side-edges 208, 209, a front waist edge 210 and a rear waist edge 211. Elastic devices 212, 213 are mounted along the longitudinally extending side-edges 208, 209 of the diaper and also along the rear waist edge 211. The diaper is secured in a pants-like configuration with the aid of two fastener tabs 215, 216 which are mounted on the longitudinally extending side edges 208, 209 in the proximity of the rear waist edge 211 and which can be fastened to a fastener receiving region 217 on the front diaper part 205, close to the front waist edge 210.

The absorbent body 203 is comprised of two layers 219, 223. The absorbent layer 219, the storage layer 219, located proximal to the liquid-permeable casing sheet 201 is comprised of a coarse-stitch knitted, braided or woven net 226 of material which will swell in the thickness direction of the diaper, i.e. in its Z direction, when wetted. The material may, for instance, have the form of threads, bands or strips which include a superabsorbent, gel-forming material. Another conceivable material is threads or bands coated with a polymer mixture which when wetted will ferment and form a shape-stable foam on the bands or threads. As seen in a direction away from the liquid-permeable casing sheet 201, there is included beneath the storage layer 219 a liquid-dispersion layer 223 of the same kind as that described with reference to the diapers shown in FIGS. 1–5.

If so desired, it is also possible, of course, to provide the diaper of FIG. 6 with a soft, coarse-pore liquid-receiving absorption layer between the liquid-permeable casing sheet 201 and the storage layer 219.

Figure 7:
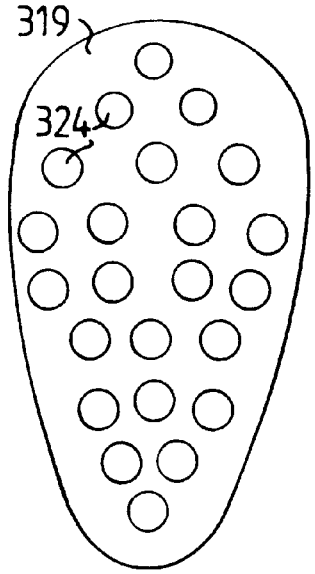
FIG. 7 illustrates an inventive storage layer which includes a plurality of through-penetrating holes.

FIG. 7 illustrates an alternative embodiment of a storage layer 319 comprised of a material which can swell in the Z direction. The storage layer 319 includes a plurality of through-penetrating circular holes 324 which function as liquid take-up reservoirs. The storage layer 319 is intended for use as a single absorbent layer, or may be used together with a further absorption layer in an absorbent article, such as a diaper, a sanitary napkin, an incontinence guard or equivalent article. When the storage layer is wetted, the layer will swell in the Z direction, i.e. in the thickness direction, causing the volume of the holes 324 to increase and therewith also their liquid accommodating capacity.

The highest concentration of holes 324 in the storage layer 319 lies within the area of the layer that is intended to be placed in the primary wetting area of the absorbent article. Since the holes 324 are not connected mutually, no liquid can flow freely between the holes and spreading of the liquid in the XY plane of the absorption layer 319 is effected by capillary transportation in the absorption material between the holes 324. There is therefore no real reason to arrange holes 324 at an excessively long distance from the primary wetting area.

FIG. 8 shows a further storage layer 419 for use in absorbent articles. The storage layer shown in FIG. 8 has been formed from a web of material which has been cut longitudinally along a sinusoidal curve 427, whereafter the two web halves 428, 429 have been displaced in relation to one another through a distance of one-half wavelength in the long direction of the web. There is thus formed in the longitudinal centre part of the web, holes 424 which alternate with overlapping web parts 430. Similar to the case in the earlier described embodiments, the material in the storage layer 419 is a material which will swell in the thickness direction of the material, i.e. in the Z direction, when wetted.

FIG. 9 illustrates an example of a further web which includes holes 524. The holes are formed by first cutting the web 519 in two, longitudinally in a curved pattern, and then displacing the separated web parts longitudinally so as to obtain a repeated pattern of openings 524 and overlapping parts 530 in the web. The web 519 shown in FIG. 9 has been cut longitudinally to form two generally sinusoidal curves 527. Subsequent to displacing the edge parts 528, 529 of the web in relation to its centre part 531, there is obtained two longitudinally extending rows of holes 524 with intermediate overlapping parts 530. Of course, the principle can be applied to produce any number of rows of openings in a web of material. The number of rows of holes is determined in this regard by the number of curve-shaped cuts made in the web.

Figure 10:
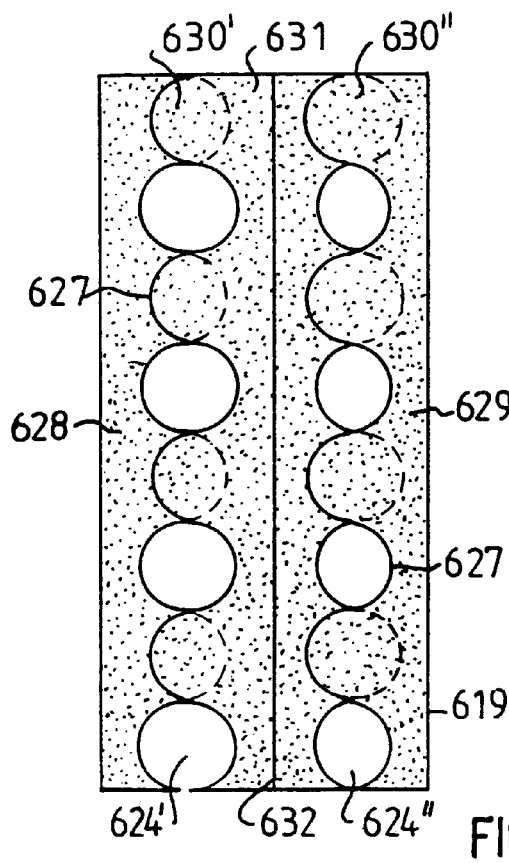
FIG. 10 illustrates a storage layer having two rows of holes of different sizes.

The web of material 619 shown in FIG. 10 has been cut in two longitudinally in the same way as the web 519 in FIG. 9. One edge part 628 of the web 619 has then been displaced longitudinally and. transversely away from the longitudinal centre line 632 of the web 619. The other edge part 629 has been displaced both longitudinally and transversely in towards the longitudinal centre line 632 of the web 619. This enables the size of the holes 624', 624" and the size of the overlapping parts 630', 630" to be adjusted. When an edge-part 629 is displaced towards the longitudinal centre line 632 of the web 619, the size of the holes 624" is decreased while, at the same time, obtaining a larger overlap 630" between the web parts located between the holes. The size of the holes 624' is increased correspondingly, by displacing the edge-part 628 of the web 619 away from the centre line 632.

Figure 11:
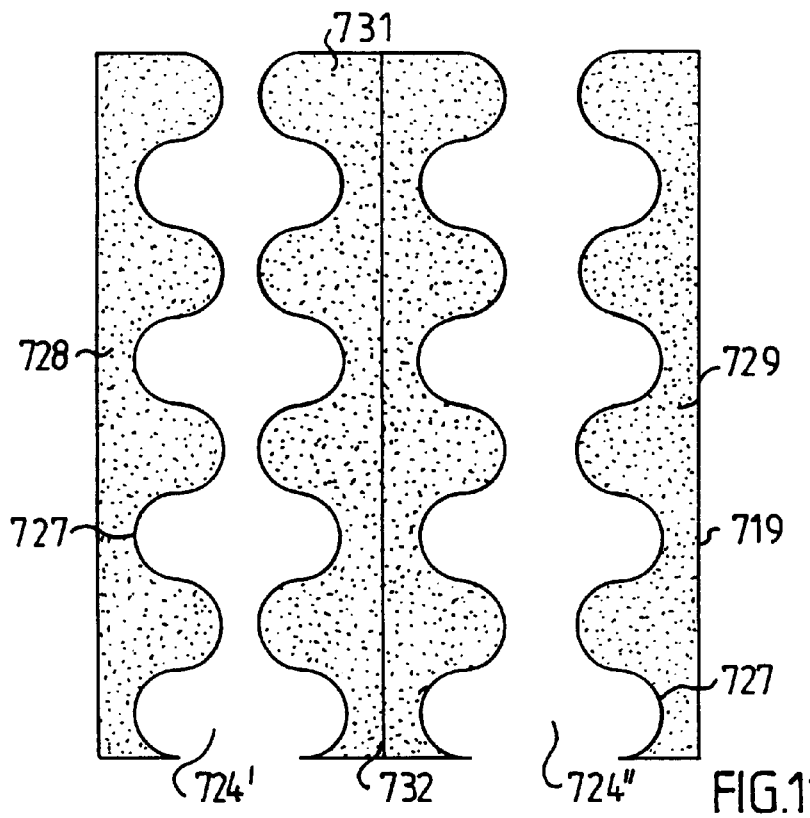
FIG. 11 illustrates a storage layer having undulating, channel-like cavities.

FIG. 11 illustrates how continuous longitudinally extending openings can be obtained between parts of a web 719 that has been cut along generally sinusoidal curves 727. The web parts 728, 729, 731 in FIG. 11 are mutually displaced both in the longitudinal and transverse directions of the web 719, by moving the cut edge-parts 728, 729 laterally in a direction away from the longitudinal centre line 732 of the web 719. The width of the continuous opening 724', 724" between two web parts is determined by the distance through which the web parts are moved apart. FIG. 11 shows two examples of openings 724', 724" of mutually different widths. Of course, the web 719 may include any desired number of continuous openings of the kind described here.

The web parts can be placed in the article with the curved cuts either in the longitudinal or in the transverse direction of the article. Curve forms other than sinusoidal curves may be chosen selectively, such as sawtooth shapes or square-wave shapes.

Holes of varying sizes can be obtained when the waves have different amplitudes along the curve, for instance such that the holes in the wetting area will be larger than the holes outside this area. Waves of varying wavelengths can also be chosen, resulting in a varying overlap between the holes with a given displacement between the web parts.

Although the invention has been described in the aforegoing mainly with reference to diapers, it will be understood that the invention can be applied to all types of absorbent articles intended for the absorption of body liquids or fluids. Examples of such articles are diapers and incontinence guards for children and adults, sanitary napkins, panty guards, bed protectors, seat protectors, wound dressings and like articles.

Neither is the invention restricted to the here described shapes and sizes of holes, grooves and swellable bodies, since a number of further embodiments are conceivable in this regard. For instance, holes formed in a storage layer may have any suitable shape or form whatsoever. Naturally, different shapes and sizes of holes and grooves or channels may be combined in one and the same article. The swellable bodies disposed as "columns" in a continuous cavity may, of course, vary in both size and shape, and are not restricted to the cylindrical bodies described and illustrated.

An absorbent body may also contain more than one storage layer. In this regard, additional storage layers may be of the same kind as the first storage layer or may differ from the first storage layer by virtue of material choice or construction.

We claim:

1. An absorbent article which includes a liquid-permeable inner casing sheet disposed on a first surface of the article, a liquid-impermeable outer casing sheet disposed on a second surface of the article, and an absorbent body which is enclosed between said inner and outer casing sheets and which includes a storage layer comprising at least one cavity or region of lower density than the density of a portion of said storage layer located adjacent said cavity or region and extending generally in the same plane thereas, wherein said portion of the storage layer includes a material which, when wetted, increases the volume in a direction generally perpendicular to said first surface of the article, whereby the size of said cavity or region also increases in said direction as a result of the article being wetted.

2. An article according to claim 1, wherein said cavity is comprised of one or more holes or regions of lower density than the density of said material in said storage layer, said holes or regions extending through at least a portion of a thickness of said storage layer.

3. An article according to claim 1, wherein said storage layer is disposed between a first receiving layer and a third liquid dispersion layer, said storage layer including at least two spaced bodies of material which extend in the form of column-like spacing means essentially perpendicularly between said first receiving and said third liquid dispersion layers, delimiting said cavity therebetween.

4. An article according to claim 3, wherein said bodies of material in said storage layer are comprised of superabsorbent material enclosed in tubular casings which extend between said first receiving and said third liquid dispersion layers, whereby swelling of the superabsorbent material by gel formation upon absorption of body liquid can only take place within the tubular casings in a direction which is generally perpendicular to said first and second surfaces of the article.

5. An article according to claim 1, wherein said cavity is channel-like and extends in the longitudinal direction of the article.

6. An article according to claim 1, wherein said storage layer is formed from a web of material which is divided in the longitudinal direction of the web along an undulating curve which crosses a line extending in the longitudinal direction of the web at least two times thereby forming alternating web portions and web cavities along the longitudinal direction of said web.

7. An article according to claim 6, wherein said web is placed in the article with the undulating curve extending either in the longitudinal direction or transverse direction of the article.

8. An article according to claim 6, wherein the curve is generally sinusoidal in shape; and in that said web portions are displaced mutually in the longitudinal direction of said web by one-half of a wavelength, whereby said web portions and said web cavities are generally circular or oval.

9. An article according to claim 6, wherein the curve is sawtooth shaped, square-wave shaped or has some other desired shape.

10. An article according to claim 6, wherein waves of the undulating curve have a varying amplitude, such that said web cavities defined between said web portions will vary in size.

11. An article according to claim 6, wherein said storage layer includes a channel-like undulating space which extends between said web portions, said undulating space being obtained by moving said web portions away from each other in the transverse direction of said web.

12. An article according to claim 1, wherein said storage layer is comprised of a particle material which includes flash-dried cellulose fibres that have been dry-formed to a web having a surface weight of 30–2000 g/m$^2$ and compressed to a density of between 0.2–1.2 g/cm$^3$, said web having been incorporated in the article without subsequent defibration and fluff formation.

13. An article according to claim 1, wherein said storage layer is formed from an air-laid web of cellulose fibres which has been compressed to a dry-formed sheet having a first density of between 0.2–1.2 g/cm$^3$ and which has thereafter been softened mechanically to obtain a second density lower than the original density and has therewith been delaminated, such as to form a plurality of incompletely separated thin fibre layers which per se have a density which corresponds to the first density.

14. An article according to claim 1, wherein said storage layer is formed from a material portion having a first thickness and comprising resilient material, said material portion having been compressed perpendicular to a plane through said material portion to a second thickness and having been bound in its compressed state with a binder that is dissolvable in body liquid, wherein bonding of said material portion ceases when said material portion is wetted and said storage layer returns at least partially to the first thickness.

15. An article according to claim 14, wherein said storage layer is formed from a compressed foam material which expands in the direction of its thickness when wetted.

16. An article according to claim 14, wherein said storage layer is formed from a compressed fibre layer which is comprised at least partially of fibres which have a given resiliency in a wet state.

17. An article according to claim 1, wherein said cavity of said storage layer is largest within a primary wetting area of the article, the primary wetting area being an area of the article which is intended to be first wetted by body liquid.

18. An article according to claim 17, wherein a volume of said cavity of said storage layer decreases in a direction away from said primary wetting area.

19. An absorbent body for use in an absorbent article which includes a liquid receiving layer comprised of soft, preferably resilient material having a high liquid permeability and low liquid dispersion capacity, and a liquid storage structure disposed inwardly of the first layer, wherein said liquid storage structure includes a storage layer which presents a receiving space in which body liquid is taken-up and which is comprised of at least one cavity or region of lower density than the density of the remainder of the storage layer, wherein parts of said storage layer adjacent said receiving space include a material which when wetted increases in volume in a direction generally perpendicular to a plane of said storage layer, whereby the size of said receiving space also increases in said direction when the article is wetted; and in that said liquid storage structure also includes a liquid-dispersion layer comprised of material having a high liquid dispersion ability, wherein said storage layer is disposed between said receiving layer and said liquid dispersion layer.

* * * * *